United States Patent [19]

Buzzi et al.

[11] Patent Number: 4,865,025

[45] Date of Patent: Sep. 12, 1989

[54] DRILL GUIDE AIMING DEVICE FOR MEDULLARY RODS

[76] Inventors: Carlo Buzzi, Stauffacherstrasse 98, CH-8004 Zürich; Alexandre de Couët, Weinbergstrasse 115, CH-8006 Zürich, both of Switzerland; Mohamed Hamid, 18, rue du Canal de la Marne, F-67300 Schiltigheim, France

[21] Appl. No.: 224,286

[22] Filed: Jul. 25, 1988

Related U.S. Application Data

[63] Continuation of Ser. No. 809,805, Dec. 16, 1985, abandoned.

[30] Foreign Application Priority Data

Dec. 26, 1984 [FR] France .................. 84 19956
Jan. 16, 1985 [FR] France .................. 85 00881

[51] Int. Cl.$^4$ .............................................. A61F 5/04
[52] U.S. Cl. ................... 128/92 VD; 128/92 R; 128/92 YY
[58] Field of Search .......... 623/23; 128/92 VD, 92 Y, 128/92 YZ, 92 YY, 92 YE, 92 VY, 92 VC, 665, 92 VV, 92 R

[56] References Cited

U.S. PATENT DOCUMENTS

| | | |
|---|---|---|
| 2,666,430 | 1/1954 | Gispert . |
| 2,697,433 | 12/1954 | Zehnder . |
| 3,670,724 | 6/1972 | Bosacco .................. 623/23 X |
| 3,674,008 | 7/1972 | Johnson .................. 128/665 |
| 3,814,089 | 6/1974 | Deyerle .................. 623/23 X |
| 4,033,043 | 7/1977 | Cunningham . |
| 4,281,649 | 8/1981 | Derweduwen ........... 128/92 VD X |
| 4,418,422 | 11/1983 | Richter et al. ........... 128/92 VD X |
| 4,476,870 | 10/1984 | Peterson et al. ................ 128/665 X |
| 4,519,100 | 5/1985 | Wills et al. ................ 128/92 YZ X |
| 4,541,424 | 9/1985 | Grosse et al. ................ 128/92 VD |
| 4,567,882 | 2/1986 | Heller ............................ 128/665 X |
| 4,600,011 | 7/1986 | Watmough ..................... 128/665 X |
| 4,611,586 | 9/1986 | Agee et al. ................. 128/92 VD X |
| 4,621,628 | 11/1986 | Brudermann .................. 128/92 VD |
| 4,644,943 | 2/1987 | Thompson et al. ........ 128/92 VD X |
| 4,667,664 | 5/1987 | Taylor et al. ............. 128/92 YY X |

FOREIGN PATENT DOCUMENTS

| | | |
|---|---|---|
| 0086883 | 12/1982 | European Pat. Off. . |
| 2425840 | 5/1979 | France . |
| 2524296 | 10/1983 | France . |
| 0825047 | of 1981 | U.S.S.R. ........................ 128/92 VD |
| 0992045 | 2/1983 | U.S.S.R. ........................ 128/92 YY |

OTHER PUBLICATIONS

Current Medical Diagnosis & Treatment (1985), Lange Medical Publications, p. 115.
Current Pediatric Diagnosis & Treatment, 8th edition, Lange Medical Publications, p. 48.
Clinics in Perinatology, vol. 12/No. 1, Feb. 1985, Symposium on Noninvasive Neonatal Diagnosis, pp. 3–20.

*Primary Examiner*—Richard J. Apley
*Assistant Examiner*—David J. Bender

[57] ABSTRACT

The apparatus of the invention enables positioning a drilling guide parallel to the axes of transversal holes in the broach without seeing the holes. To this effect the drilling guide is adjustable with one degree of freedom on a mounting, the adjustment being effected as a function of positional information relating to the axis of the hole and sensed by mechanical feeler means which may be inserted into the broach. After this positioning is done by the apparatus according to the invention, a translation of the drilling guide may be done quickly by any conventional means in order to compensate for the distance between the axis of the drilling guide and the axis of the hole.

4 Claims, 8 Drawing Sheets

DRILL GUIDE AIMING DEVICE FOR MEDULLARY RODS

This is a continuation of application Ser. No. 809,805, filed Dec. 16, 1985, now abandoned.

This invention concerns an apparatus intended to be employed in the course of fastening a broach into a fractured bone.

BACKGROUND OF THE INVENTION

Osteosynthesis operations are practised at the present time with the help of rigid elements which are associated with the fractured bone in order to reinforce it and to restore as quickly as possible to the patient his faculties of movement. These reinforcing elements are formed for instance by plates fixed to the outer surface of the bone on either side of the fracture or by hollow pins or broaches which are inserted in the medullary canal of the bone. The latter elements are employed more and more often since they are the least traumatizing for the patient and enable a rigidification of the fractured bone, the broach resisting not only compressive and tensile forces, but also torsional forces. It is this latter property of the broaches which may be obtained only if they are fixed not only longitudinally, but also in rotation about their axis, particularly in certain types of fractures called "low" or "high" (diaphyso-epiphyseric fractures). Consequently, if the broach must resist twisting, it is necessary to place transversal screws which pass diametrically through the bone as well as one or several pairs of aligned holes usually provided close to the distal end of the broach. This practise is above all applied in cases where the fractured bone is the femur or tibia.

The broaches are of themselves known. They generally exhibit a cross-section having a form approximately trefoiled, one of the ends being slightly splayed and provided with interior threading, the other end being slightly tapered in order to facilitate insertion into the medullary canal. Moreover, according to the type of application, the broach may be somewhat curved along its longitudinal axis and exhibit longitudinally a slot over its entire length, which gives it a certain flexibility in bending, this permitting at the time of insertion a perfect adaptation to the form of the medullary canal. As is well understood, the surgeon has available a choice among various lengths and diameters which are determined by the bone to be treated and the dimensions of the limb of the patient.

According to the present day technique, the surgeon initially puts the broach in place according to a known procedure, then proceeds to locate the transversal holes found at the distal end of the broach. To this effect he has available a locating apparatus employing X-rays by means of which he may indicate on the skin of the limb the place where the axis of the holes traverses the skin, then after having made an incision he pierces a hole by the aid of a drill passing via the holes of the broach. Thereafter, the screw may be fixed in place.

This process accordingly necessitates working with X-rays to which are exposed the patient as well as the operating room personnel. The locating operation requires approximately two hours and one must count on an exposure of approximately 400 to 1000 REM per operation. This important dose, to which is exposed the personnel each time that an operation is carried out, presently leads to hesitation among surgeons for the employment of this method, such surgeons preferring either to utilize plates or broaches not having transversal screws for reinforcement purposes.

The prolonged duration of the employment of the apparatus in the course of an operation naturally prevents its use for operations which might otherwise be realized at the same time in an operating room of the hospital other than that in which the operation under consideration takes place. This requires a very close programming of operations which is undesirable, particularly if there are emergencies.

The invention thus has as its purpose to provide an apparatus for marking it easier to locate in situ transversal holes in a hollow broach implanted in the medullary canal for the retention of the fragments of a fractured bone. More precisely, the invention provides an apparatus for rapidly positioning a drilling guide parallel to the axis of the transversal holes. The compensation of the distance between the axis of the drilling guide and the axis of a hole may thereafter be done quickly by conventional means.

SUMMARY OF THE INVENTION

In accordance with the invention, there is provided an apparatus for in situ positioning a directing guide parallel to the transversal holes in a hollow broach implanted in the medullary canal of a bone for retaining the fragments thereof following fracture, said broach being provided with fastening means for said apparatus at its proximal end, the hole or holes to be located being provided at least at its distal end, said apparatus comprising a support intended to be mounted on said broach utilising said fastening means;

a drilling guide defining an axis to be brought parallel to the axis of the hole;

a mounting fixed to said support and bearing said drilling guide in a manner to permit thereto one degree of freedom relative to the broach, which is a rotation thereabout in a plane containing the axis of the hole mechanical measuring means for providing information concerning the direction of the hole axis adjusting means for bringing the axis of said drilling guide into the same direction as the axis of the hole as a function of said information.

Thanks to these characteristics, a locating operation may be completed after only a few minutes by a two stage process in which the first stage is done with the apparatus according to the invention. This constitutes a substantial time gain which may be very important when one is concerned with patients suffering multiple injuries.

The invention will be better understood in its various forms in referring to the attached drawings.

DESCRIPTION OF THE PREFERRED EMBODIMENT

Figure 1:
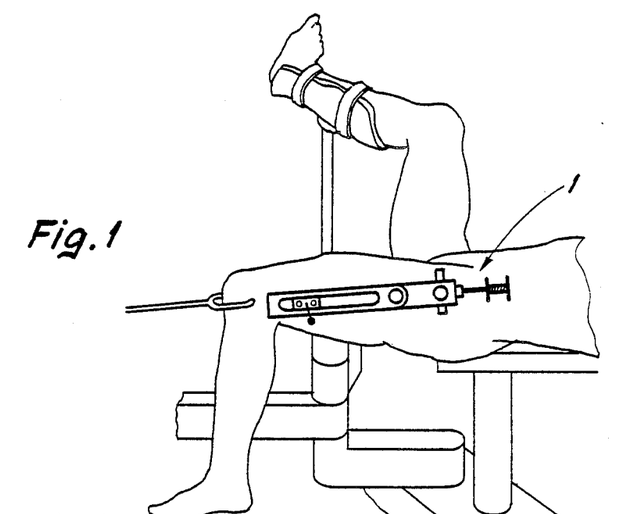
FIGS. 1 and 1A show a schematic representation of the position of the apparatus according to the invention in the course of an operation for the retention of a fracture of the femur.
Figures 1A, 2, 2A:
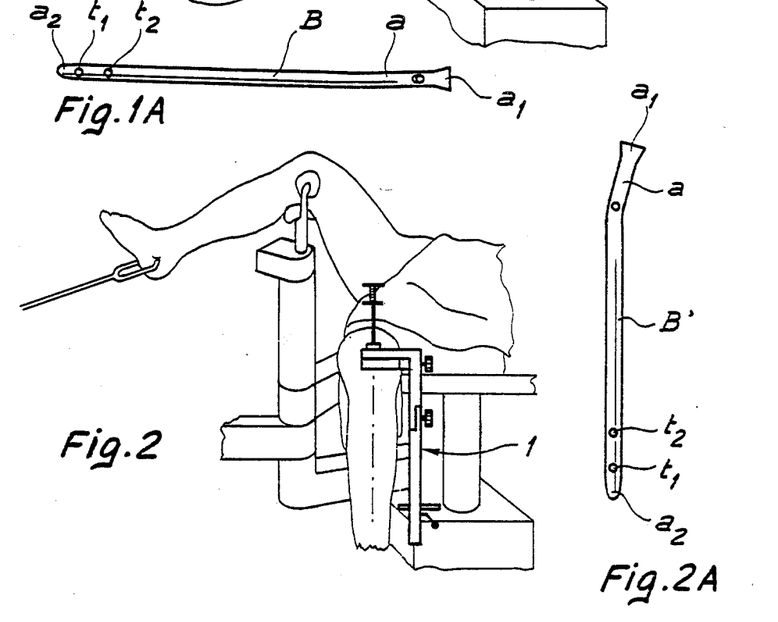
FIGS. 2 and 2A show analogous views to those of FIGS. 1 and 1A in the case of the retention of a fracture of the tibia.

FIGS. 1 and 1A show the case of an osteosynthesis operation on the femur, FIG. 1 showing the position of the apparatus in accordance with the invention, generally designated by reference 1 during the locating of a transversal hole provided in a pin or broach which has already been placed in the medullary canal of the femur.

FIG. 1A shows an example of a broach in itself well known capable of being employed for an osteosynthesis operation to which the apparatus according to the invention may be applied. It is seen that such broach B comprises a stem which is formed of metal inert to human body tissues and fluids. This stem is hollow and has a cross-section approximately trefoiled which confers thereon a certain flexibility so that the stem may adapt itself perfectly to the form of the medullary canal when it is placed into the bone. It will be here thus noted that not only does the stem not have a rectilinear form, but moreover in the course of its setting into place in the bone it permits a certain deformation not known a priori.

The broach B exhibits a proximal end a provided with a splayed mouth a1 having threading on the interior thereof. At the time of its insertion this proximal end accommodates initially an anvil which is screwed into the threaded hole and on which the surgeon may strike for facilitating the introduction thereof. At its opposed end a2, the broach B includes two transversal holes t1 and t2 which are intended to receive blocking screws (not shown on the figures) which generally are supplied with the broach B.

As may be well understood, broaches are furnished in various dimensions, both length and diameter, as is well known to specialists.

FIGS. 2 and 2A show the case of an osteosynthesis operation on the tibia, FIG. 2A showing the form of a broach B' employed in this case. It is seen that this broach has a bent proximal end with a splayed mouth as in the case of the broach intended for the femur. Moreover, at the outside of the elbow this broach B' includes an aperture which is not visible on the drawing. For the remainder, broaches B and B' are of identical form.

It is also to be noted that during insertion of the broach into the bone to be retained, it undergoes a deformation in torsion, the broach "worming" itself in a certain manner into the medullary canal in view of its external form, this increasing particularly the rigidity of the assembly constituted by the broach and the bone.

In other words, holes t1 and t2 which are to be located do not conserve relative to the splayed mouth either the axial position or the position in the radial plane relative to the mouth, this evidently complicating the locating operation, it being understood that following the insertion, the holes are no longer visible.

Figure 3:
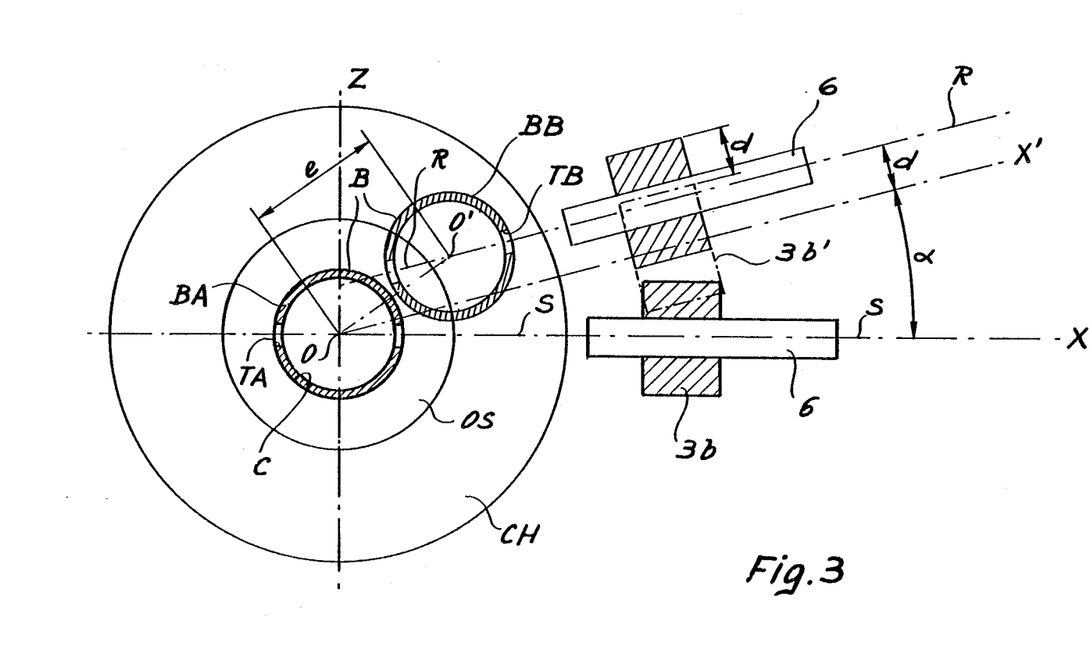
FIG. 3 is a diagram permitting the analysis of the principle which is at the basis of the present invention.

Reference will now be had to FIG. 3 which shows the principle of operation of the apparatus in accordance with the invention, this representation being equally applicable to the operations of FIGS. 1 and 2 and as may well be understood, to other operations which may be effected by osteosynthesis.

This figure shows schematically the bone OS surrounded by flesh CH and provided with a medullary canal C.

Figure 4:
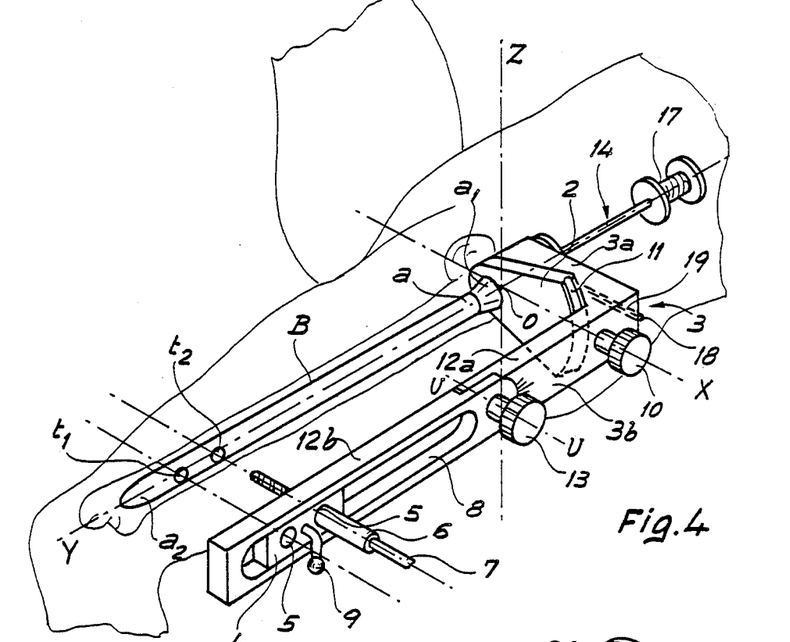
FIG. 4 is a schematic representation in perspective to a larger scale relative to FIGS. 1 and 2 of a first form of the invention.

However, before describing in detail FIG. 3, reference will initially be had to FIG. 4 in order to become acquainted with the different main elements of the apparatus according to the invention which, as may be seen, is here employed for the retention of the fracture of the bone of the femur. There will be recognized a broach B with its proximal end a and its distal end a2, the two transversal holes t1 and t2 as well as the splayed mouth a1 provided with its interior threading. On this mouth is screwed a support 2 which comprises the element of the apparatus remaining fixed during the locating operation. This support which, in the example shown, has the form of a sector of a circle, defines a plane XOZ (here vertical) in which is situated a point O considered as the origin of the coordinate system XYZ and which is a reference system in the description which is to follow. The origin O of this system of coordinates is situated on the OY axis constituting at this point a tangent to the axis of the broach B which as already indicated hereinabove, is not a straight line, but a line more or less curved following the form of the broach to the origin and equally as a function of the deformations which such broach undergoes during its insertion into the bone.

The apparatus likewise includes a corner angle 3 for adjustment which is articulated on support 2 around the OY axis.

The corner angle 3 includes a first branch 3a extending perpendicular to the axis OY as well as a second branch 3b which extends parallel to this axis over the length of broach B when the apparatus is in place for measurement.

On branch 3b is movably mounted along its longitudinal axis a slider 4 provided with two transversal passages 5 intended to receive a drilling guide 6. This latter is dimensioned to be able to receive a piercing bit 7 adaptable to a surgical drill (not shown). The slider 4 may be displaced in a longitudinal glide channel 8 in branch 3b whilst being capable of being clamped in such channel by a locking mechanism (not shown) which one may operate by means of a handle 9.

Corner angle 3 which is thus articulated in rotation about axis OY on support 2 may be clamped relative to the latter thanks to screw 10 which acts on the circular edge 11 of such support 2 (see likewise FIGS. 5A and 5B to which reference will be made subsequently). Moreover, branch 3b is realized in the form of an articulated knee lever and is thus itself divided into a first portion 12a proximate the arm 3a as well as a portion 12b in which is provided the glide channel 8, the joint of the articulated lever (axis U-U) being clamped and released by a screw 13. This articulated knee lever is not used in the positioning operation according to the invention. It is used in a later stage of the complete locating operation.

Figure 8:
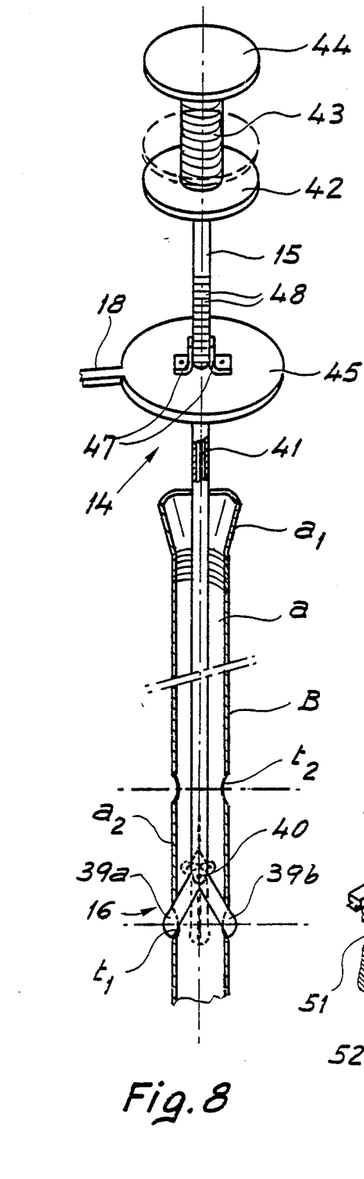
FIG. 8 is a schematic perspective view of the mechanical feeler means employed in the apparatus according to the invention.

The apparatus further comprises mechanical feeler means 14 essentially formed by a rod 15 which may be inserted into the bore of broach B and which bears at its forward end a feeler 16 (FIG. 8) and at its other opposite end an operating member 17, these members being described subsequently in relationship to FIG. 8. It is sufficient for the moment to note that the mechanical feeler means 14 is provided with an index 18 which is intended to cooperate with a location marker 19 provided on the corner angle 3 and more precisely on the branch 3a of the latter at the surface which is not visible on FIG. 4. Nevertheless, one may note this marker 19 for instance on FIGS. 5, 7 and 10, index 18 being best seen on FIG. 5.

Referring again to FIG. 3, the drilling guide is traced in the plane XOZ and on this plane has been projected a section BA of the broach B passing through one of the transversal holes TA of the latter, in supposing that the broach is perfectly rectilinear and has undergone no deformation in the course of its insertion into the bone. The figure likewise shows the projection of the same section indicated by BB, but this time in its real position, i.e. when the broach has undergone deviation by the medullary canal, taking into account its original non rectilinear form. In order to improve the clarity of this figure, the deviation of the broach has been strongly exaggerated. It should be noted likewise that strictly seen this example refers only to a femur broach since the broach for the tibia (figure 2A) is very much bowed close to its splayed mouth; the support of the apparatus being then arranged somewhat differently (see FIG. 7). This point will be reverted to subsequently. However, the principle of the measurement resulting from FIG. 3 is equally applicable to the case of the femur as to that of the tibia.

It is evident that the center of section BA coincides with the center O of the coordinate system XYZ, the center of the section BB indicated by O′ being displaced by a distance e and the broach itself having been twisted so that the diametrical plane passing through the axis of the hole TA undergoes a rotation by an angle α to be positioned as shown for hole TB on FIG. 3. The latter represents likewise the drilling guide 6 as well as the outline of the section of branch 3b of the corner angle 3 in different positions which will now be explained.

The purpose of a locating operation is finally to place the axis S—S of the drilling guide (which is initially found effectively in coincidence with the axis O—X as shown) on the axis defined by the hole TB of the broach i.e. coincident with the axis R—R. If this operation may be obtained with precision, the surgeon will be certain to pierce the bone in such a manner that the drilling bit passes into the broach through hole TB and this without there being a necessity to see the hole. It will thus not be necessary to proceed by cutting into the flesh CH with attendant bleeding at the place where the hole TB is found.

The location is obtained in two stages which consist respectively initially and according to the invention in placing the drilling guide in a manner such that its axis S—S is situated in a plane parallel to the axis R—R and containing the axis O—Y, then shifting the drilling guide 6 in translation so that the axes R—R and S—S coincide. It will be understood through examination of FIG. 4, that the first stage is realized by causing the corner angle 3 to turn around the axis O—Y (first degree of freedom of the drilling guide), the second stage consisting of folding the articulated knee lever 12a, 12b about axis U—U (second degree of freedom), the small error introduced by the fact that this latter movement is a rotation being negligible taking into account the various dimensions of the elements in play (particularly the length of the broach). The invention is directed to an apparatus designed to carry out the first stage.

Figure 5:
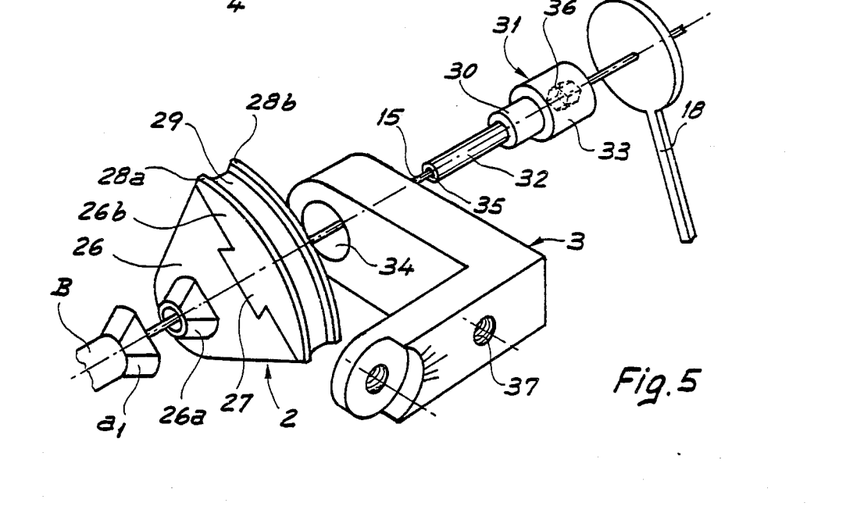
FIG. 5 is an exploded partial perspective view of the proximal portion of the apparatus according to the invention.
Figure 5A:
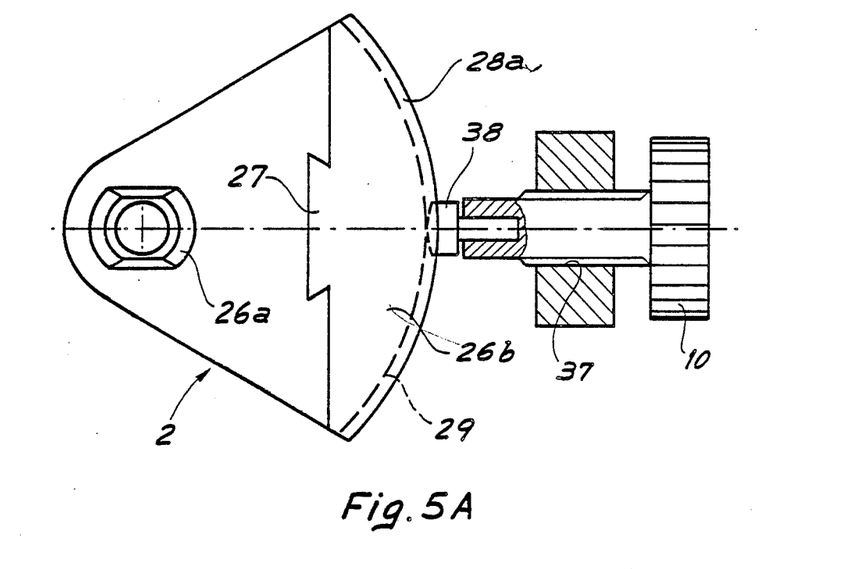
FIGS. 5A and 5B are cross-sections of a detail of the apparatus shown on FIGS. 4 and 5.
Figure 5B:
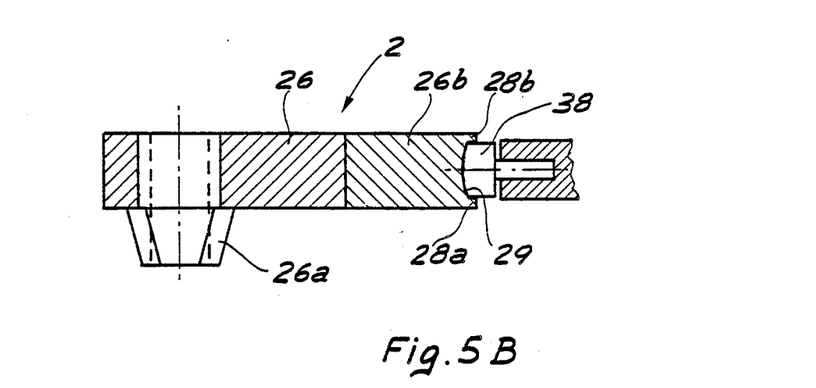

The angular shift α is measured by the use of first sensing means 14 which defines a plane in which is situated the axis of the rod 15 and the index 18 (see FIGS. 4 and 5). The feeler 16 is capable of bringing this plane into coincidence with the real axis R—R of the hole TB when it is inserted into broach B to the distance of the hole. If this axis is inclined, the index 18 will not be situated in the plane XOY of FIG. 4, but will be inclined by the angle α sought relative to the marker 19 traced on the branch 3a of the corner angle 3. To bring the index 18 into coincidence with this marker 19, it is then necessary to loosen screw 10 and to cause the corner angle 3 to turn through angle α around axis O—Y, which will place branch 3b in the position shown in dotted outline and referenced 3b′ on FIG. 3.

The mechanical feeler means 14 has then performed its task and the surgeon may remove it from broach B.

It is to be noted that the process which has just been described is exactly the same whether it concerns retention of a fracture of the femur or of the tibia, taking into account as indicated above the remarks concerning the support 2.

It will likewise be noted that the positioning operation is very simple and rapid, the surgeon being able to execute them in approximately five minutes only.

The construction of the apparatus will now be explained in greater detail through reference to FIGS. 4 to 7.

Support 2 (FIG. 5) includes a fastening plate 26 on which is arranged a stud 26a which is complementary in form to the splayed mouth a1 of broach B, this form not being of revolution whereby such plate may be clamped by simple screwing only in a single radial position relative to broach B. The plate 26 is fastened to a support plate 26b, for instance by means of a dovetail fastening 27, the circular edge of this support plate providing two lateral flanges 28a and 28b defining a groove of which the bottom is hollowed out in rounded form (see FIG. 5B at 29).

Plate 26 is provided with a hole which is intended to receive the intermediate collar 30 of a screw 31 of which one end 32 consists of a threaded joining piece adapted to the threading of the broach B and of which the opposite end 33 serves as a rotation bearing for the branch 3a of corner angle 3 when inserted into an opening 34 of this branch. Screw 31 is pierced by an axial bore 35 in order to provide a passage for the feeler means 15 and 20. The surface of the end of part 33 of screw 31 is provided with a hexagonal cavity 36 to enable the rotation thereof by means of a six-sided wrench.

The clamping screw 10 (FIG. 5A) which traverses branch 3b through a threaded hole 37 bears at its end a centering finger 38 which is intended to be brought to bear against the bottom 29 of the groove defined by the flanges 28a and 28b in order to apply corner angle 3 against plate 26. This clamping likewise assures the fixation in rotation of the corner angle relative to the plate and maintains thus the cohesion of the various members of the apparatus while making its disassembly very easy.

The mechanical feeler means 14 has been shown in detail on FIG. 8 on which will be noticed rod 15, feeler 16 and index 18 already mentioned hereinabove. At its distal end, the rod 15 bears two jaws 39a and 39b articulated around an axis 40 and urged towards the exterior thanks to a cable 41. The latter passes through rod 15 and is attached to an operating platelet 42 sliding on rod 15 against the action of a compression spring 43. This spring is supported on a counter platelet 44 transversally mounted at the end of rod 15 and fixed relative to the latter. Thus, by grasping the rod with one hand with the thumb bearing on the counter platelet 44 and two fingers hooked behind the activating platelet 42 it is possible by compressing spring 43 to bring jaws 39a and 39b together and to make them pivot around axis 40 in order to facilitate the insertion of the feeler means into broach B. When the jaws arrive at the distance of a hole t1 or t2, which the surgeon may easily determine since the length of the broach is known, he releases the platelet 42 and the jaws may enter by their rounded extremeties into the corresponding hole of the broach and thus locking rod 15 not only axially, but also in rotation, the spread apart jaws 39a and 39b defining a diametral plane in which is situated the axis of the hole concerned.

A support platelet 45 is slidingly mounted on rod 15 while being provided with springs 47 which cooperate with transversal striations 48 provided on the rod to define different lengths thereof, each position corresponding to a length of broach likely to be employed by the surgeon. Consequently, at the beginning, this platelet 45 is regulated in a manner such that the feeler means 14 is adapted to the length of the broach B to be employed. The striations 48 are thus advantageously associated with a graduation of length. The support platelet 45 bears the index 18, here constituted by a rectilinear pointer extending radially. It is this pointer which thus must be brought into coincidence with the marker 19 on the branch 3a.

It is to be noted that the radial position of index 18 corresponds to the plane defined by jaws 39a and 39b, spread apart, so that when the latter are locked in a hole in the broach the index 18 is situated in a plane in which is also found the axis of the hole concerned.

Figures 6, 7:
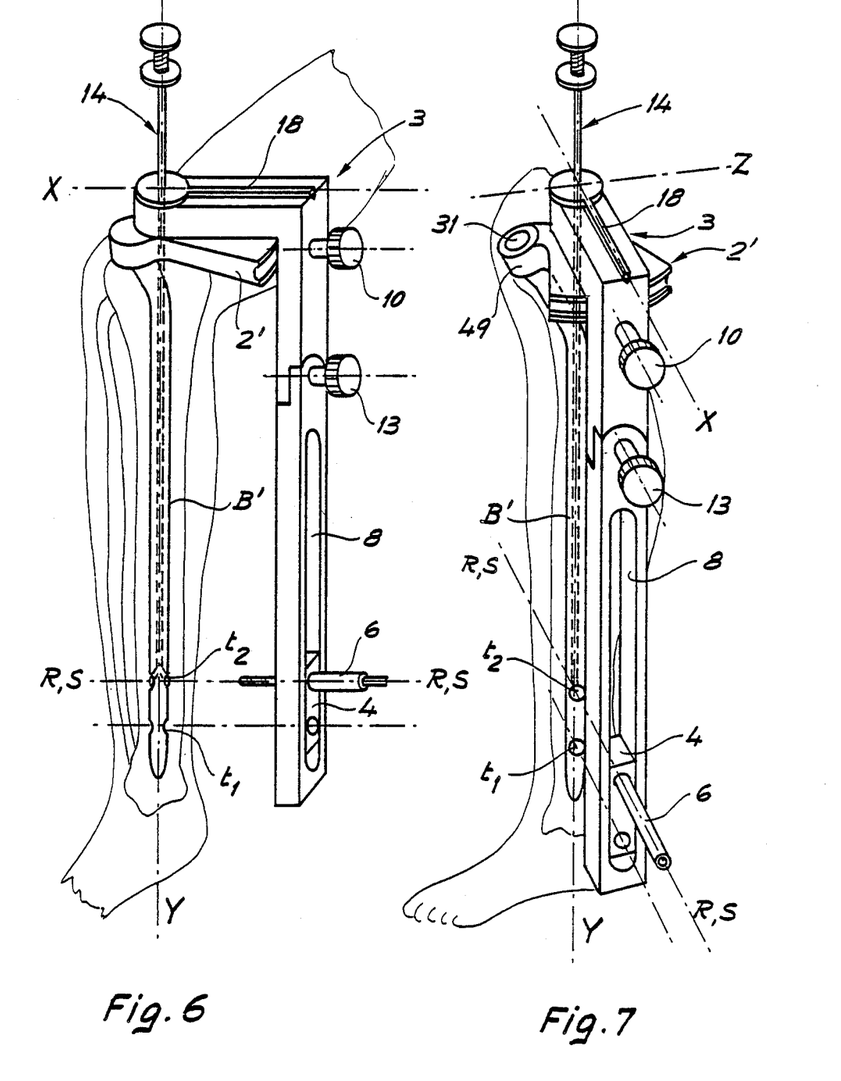
FIGS. 6 and 7 are perspective views showing in the case of the retention of a fracture of the tibia the implantation of the apparatus in accordance with the invention, the two views being taken respectively according to different angles.

FIGS. 6 and 7 show the case when location must be carried out for an operation on the tibia. Since the broaches of the tibia are provided with an inclined end (see FIG. 2A), the support for the apparatus employed in this case is somewhat different from that which has just been described. Effectively, this support, shown by reference 2', comprises a lateral lug 49 in which is inserted the fixing screw 31 (FIG. 5), this support including a passage in order to permit insertion of the feeler means 14 approximately in the alignment of broach B', this support defining, as in the previously described case, the reference plane YOZ relative to which the other locating parameters are defined. For the remainder, as much on the basis of its construction as that of its operation, the apparatus of FIGS. 6 and 7 is identical to that shown on FIG. 4.

Figure 9:
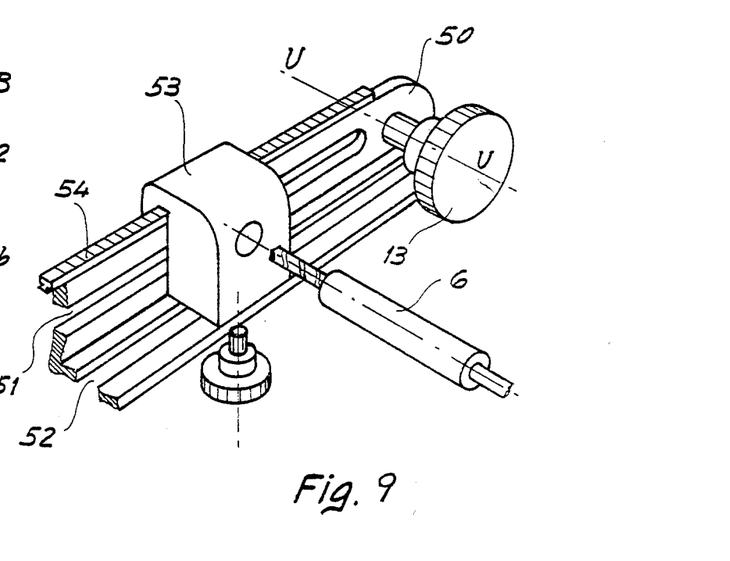
FIG. 9 is a representation in perspective of a variant of the apparatus.

There will now be described another form of part 12b of the articulated knee lever which constitutes the branch 3b of the corner angle 3 (FIG. 9). In this case portion 12b comprises a straight-edge 50 having an L-formed section of which the two branches are provided with slots 51 and 52 in which are guided a slider 53 formed so as to be able to receive the drilling guide 6. As may well be understood, straight-edge 50 may be clamped relative to the other portion 12a of the articulated knee lever, thanks to nut 13. For the remainder, it is possible to provide a graduated rule 54 mounted so as to be movable on the section of one of the branches of straight-edge 50 and intended to provide the surgeon with an indication of the length of the broach employed.

Figure 10:
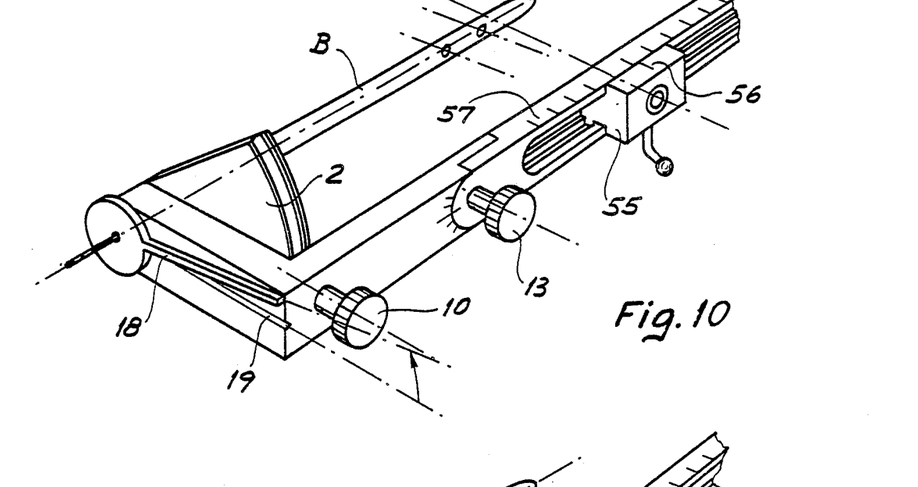
FIGS. 10 and 11 show another form of the invention respectively before and after the adjustment thereof.
Figure 11:
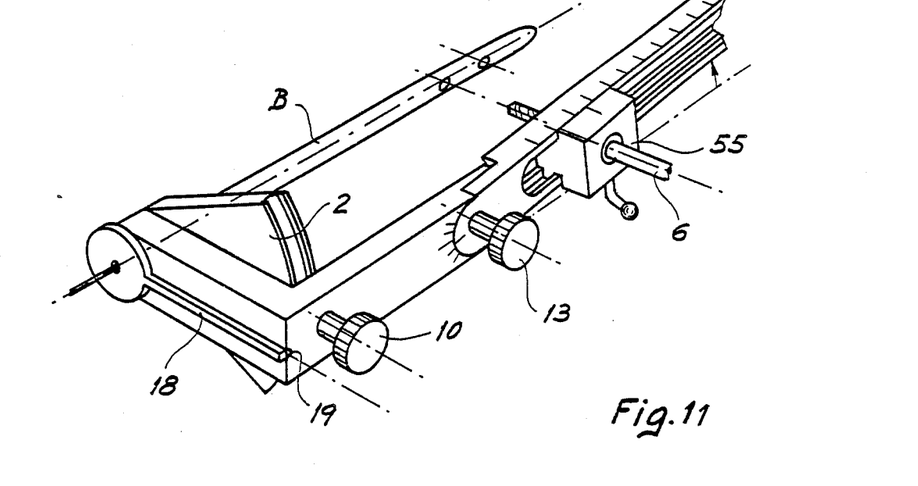

On FIGS. 10 and 11 have been shown respectively before and after its adjustment, an apparatus according to a further form of the invention. More precisely, part 12b of the articulated knee lever constituting the branch 3b of the corner angle 3 here comprises an adjustment block 55 which may be shifted proximate a graduated rule which is flush with the upper surface of said branch. In this manner, a marker 56 traced on the block may cooperate with the graduation 57 provided directly on the rule.

FIGS. 12A to 12D show several possibilities of realization of the mechanical feeler means.

Figure 12:
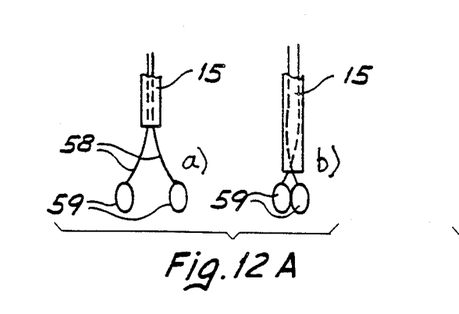
FIGS. 12A to 12D show four variants of the mechanical feeler means respectively in a and b.

On FIG. 12A, rod 15 bears at its free end two elastic feet 58 which are provided at their free ends with balls 59 capable of partially penetrating into the openings which define in each broach the axis of the transversal fastening holes. Feet 58 and balls 59 may be retracted by pulling in order to enter almost into the elongation of the contour of rod 15 at the time of the insertion of the feeler means into the broach.

The schematic view shown by FIG. 12B shows that the mechanical feeler means may also include means 60 in the form of a bellows capable of being inflated or deflated by air blown in or sucked out through a pipe 61 placed in rod 15.

FIG. 12C shows that it is likewise possible to provide at the end of rod 15 two support lugs 62 bearing at their free end cups 63 urged apart by a spring 64. These cups may be retracted as shown at B on FIG. 12C by axial traction on lugs 62 which compresses spring 64.

In the case of FIG. 12D, there are also provided cups 63 which in this case are fastened to the ends of elastic rods 65 which keep them spread apart, unless they are retracted into rod 15 by axial traction, which draws the cups into the elongation of the contour of this rod.

What we claim is:

1. An apparatus for in situ positioning a drilling guide parallel to the axis of at least one of a plurality of transversal holes in a hollow broach implanted in the medullary canal of a bone for retaining the fragments thereof following fracture, said broach being provided with fastening means for said apparatus at its proximal end, and said at least one of a plurality of holes being provided at its distal end, said apparatus comprising:
    a support adapted to be mounted on said broach utilizing said fastening means;
    a drilling guide defining an axis to be brought into coincidence with the axis of said at least one of a plurality of holes;
    a mounting fixed to said support and bearing said drilling guide in a manner to permit thereto one degree of freedom relative to the broach, which is a rotation thereabout in a plane containing the axis of said hole; measuring means for providing information concerning the direction of the the axis of said at least one of a plurality of holes, said measuring means comprising mechanical feeler means placed at the end of a rod adapted to be inserted into the broach for orienting said rod as a function of the disposition of the axis of said at least one of a plurality of holes, said rod including at its other end an index providing said information; and adjusting means for bringing the axis of said drilling guide parallel to the axis of said at least one of a plurality of holes as a function of said information.

2. An apparatus as set forth in claim 1 wherein said mounting means takes the form of a two arm corner angle, a first arm of which is mounted in an articulating manner onto said support and extends substantially perpendicularly from the broach when the apparatus is in place, the other arm extending longitudinally relative to the broach in the direction of the bone to be retained and being formed as a two element articulated lever in which the element thereof remote from the first arm bears said drilling guide in a manner permitting sliding thereof.

3. An apparatus as set forth in claim 1 wherein said mechanical feeler means comprises two sensing elements articulated on the end of the rod said elements being adapted to be arrested in said at least one of a plurality of holes in the broach whereby said rod assumes a fixed angular position representative of the direction of the axis of said at least one of a plurality of holes and is reflected in the spatial position of said index.

4. An apparatus as set forth in claim 11 wherein the index cooperates with guide marks on the mounting, said mounting taking the form of a corner angle and said guide marks being on an arm thereof extending perpendicularly from the broach.

* * * * *